US009950971B2

(12) United States Patent
Henao et al.

(10) Patent No.: US 9,950,971 B2
(45) Date of Patent: Apr. 24, 2018

(54) PROCESS AND CATALYST FOR METHANE CONVERSION TO AROMATICS

(71) Applicant: ExxonMobil Chemical Patents Inc., Baytown, TX (US)

(72) Inventors: Juan D. Henao, Houston, TX (US); Paul F. Keusenkothen, Houston, TX (US); Abhimanyu O. Patil, Westfield, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 30 days.

(21) Appl. No.: 14/738,211

(22) Filed: Jun. 12, 2015

(65) Prior Publication Data

US 2016/0023962 A1   Jan. 28, 2016

Related U.S. Application Data

(60) Provisional application No. 62/028,082, filed on Jul. 23, 2014.

(51) Int. Cl.
| | | |
|---|---|---|
| *C07C 2/76* | (2006.01) | |
| *C07C 2/82* | (2006.01) | |
| *C07C 2/84* | (2006.01) | |
| *B01J 29/78* | (2006.01) | |
| *B01J 29/72* | (2006.01) | |
| *B01J 29/70* | (2006.01) | |
| *B01J 29/48* | (2006.01) | |
| *B01J 29/42* | (2006.01) | |
| *B01J 29/40* | (2006.01) | |

(52) U.S. Cl.
CPC ............... *C07C 2/84* (2013.01); *B01J 29/405* (2013.01); *B01J 29/42* (2013.01); *B01J 29/48* (2013.01); *B01J 29/7088* (2013.01); *B01J 29/7276* (2013.01); *B01J 29/7876* (2013.01); *C07C 2523/02* (2013.01); *C07C 2523/04* (2013.01); *C07C 2523/06* (2013.01); *C07C 2523/08* (2013.01); *C07C 2523/10* (2013.01); *C07C 2523/14* (2013.01); *C07C 2523/18* (2013.01); *C07C 2523/28* (2013.01); *C07C 2523/30* (2013.01); *C07C 2523/36* (2013.01); *C07C 2523/42* (2013.01); *C07C 2523/44* (2013.01); *C07C 2523/50* (2013.01); *C07C 2523/72* (2013.01); *C07C 2523/745* (2013.01); *C07C 2523/755* (2013.01); *C07C 2529/40* (2013.01); *C07C 2529/42* (2013.01); *C07C 2529/48* (2013.01); *C07C 2529/70* (2013.01); *C07C 2529/72* (2013.01); *C07C 2529/78* (2013.01); *Y02P 20/52* (2015.11)

(58) Field of Classification Search
CPC ................ C07C 2/76; C07C 2/82; C07C 2/84
USPC .............................. 585/407, 418, 419, 420, 421
See application file for complete search history.

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| 3,832,449 A | 8/1974 | Rosinski et al. | |
| 4,016,218 A | 4/1977 | Haag et al. | |
| 4,016,245 A | 4/1977 | Plank et al. | |
| 4,076,842 A | 2/1978 | Plank et al. | |
| RE29,948 E | 3/1979 | Dwyer et al. | |
| 4,229,424 A | 10/1980 | Kokotailo | |
| 4,234,231 A | 11/1980 | Yan | |
| 4,439,409 A | 3/1984 | Puppe et al. | |
| 4,443,644 A | 4/1984 | Jones et al. | |
| 4,556,477 A | 12/1985 | Dwyer | |
| 4,826,667 A | 5/1989 | Zones et al. | |
| 4,954,325 A | 9/1990 | Rubin et al. | |
| 5,026,945 A | 6/1991 | Campbell | |
| 5,236,575 A | 8/1993 | Bennett et al. | |
| 5,245,124 A | 9/1993 | Miremadi et al. | |
| 5,250,277 A | 10/1993 | Kresge et al. | |
| 5,336,825 A | 8/1994 | Choudhary et al. | |
| 5,362,697 A | 11/1994 | Fung et al. | |
| 5,609,751 A * | 3/1997 | Wall .................. | B01J 29/405 208/133 |

(Continued)

FOREIGN PATENT DOCUMENTS

| | | |
|---|---|---|
| EP | 0293032 | 11/1988 |
| WO | 97/17290 | 5/1997 |

(Continued)

OTHER PUBLICATIONS

Baerns, "Basic Solids as Catalysts for the Oxidative Coupling of Methane," Methane Conversion by Oxidative Processes, pp. 382-402 (1992).
Ito et al., "Synthesis of ethylene and ethane by partial oxidation of methane over lithium-doped magnesium oxide," Nature, vol. 314, pp. 721-722 (1985).
McCarty et al., "Models Of The Direct Catalytic Partial Oxidation Of Light Alkanes," New Developments in Selective Oxidation, pp. 405-415 (1990).
Otsuka et al., "Synthesis Of Ethylene By Partial Oxidation Of Methane Over The Oxides Of Transition Elements With LiCl," Chemistry Letters, pp. 903-906 (1986).
Sinev et al., "Basicity Of Oxide Catalysts For Oxidative Condensation Of Methane," Translated from Kinetika i Kataliz, vol. 32, No. 1, pp. 157-1962 (1989).

(Continued)

Primary Examiner — Thuan D Dang

(57) ABSTRACT

A process and catalyst for use therein for the production of aromatics via the oxidative coupling of methane and methane co-aromatization with higher hydrocarbons in a single reaction stage. First, methane is partially converted to ethane and ethylene on an OCM catalyst component, and the OCM intermediate mixture containing methane, ethane and ethylene is subsequently converted into aromatics on an aromatization catalyst component. The reaction may be conducted at 550-850° C. and at about 50 psig. The claimed process and catalyst used therein achieves high methane conversion at lower temperatures (less than 800° C.), higher methane conversion into the aromatic products and significant reductions in production cost when compared to the traditional two (or more) step processes.

19 Claims, No Drawings

(56) References Cited

U.S. PATENT DOCUMENTS

| | | | |
|---|---|---|---|
| 5,625,103 | A | 4/1997 | Abichandani et al. |
| 5,633,417 | A | 5/1997 | Beck et al. |
| 5,675,047 | A | 10/1997 | Beck et al. |
| 5,936,135 | A | 8/1999 | Choudhary et al. |
| 6,077,498 | A | 6/2000 | Diaz Cabanas et al. |
| 6,083,867 | A * | 7/2000 | Wu .................... B01J 23/18 502/224 |
| 6,096,934 | A | 8/2000 | Rekoske |
| 7,453,018 | B2 | 11/2008 | Dakka et al. |
| 7,977,519 | B2 | 7/2011 | Iaccino et al. |
| 8,138,384 | B2 | 3/2012 | Iaccino et al. |
| 2012/0083637 | A1 | 4/2012 | Clem et al. |

FOREIGN PATENT DOCUMENTS

| | | |
|---|---|---|
| WO | 2005/005042 | 1/2005 |
| WO | 2011/149996 | 12/2011 |

OTHER PUBLICATIONS

Sinev et al., "*Kinetics Of Oxidative Condensation Of Methane In The Presence Of 40% PbO/Al$_2$O$_3$ Catalyst. I. Kinetics of Oxidation of Methane,*" Translated from Kinetika i Kataliz, vol. 30, No. 4, pp. 855-859 (1989).

Sinev et al., "*Kinetic Peculiarities Of Oxidative Condensation Of Methane On Oxide Catalysts An A Heterogeneous-Homogenous Process,*" Translated from Kinetika i Kataliz, vol. 28, No. 6, pp. 1376-1381 (1987).

Van Den Oosterkamp, "*Synthesis Gas Generation—Industrial,*" Encyclopedia of Catalysis, vol. 6, pp. 1-39 (2003).

Li et al. (Li et al., "Combined single-pass conversion of methane via oxidative coupling and dehydroaromatization," *Catalysis Letters*, vol. 89, pp. 275-279, 2003).

Anshits, A.G. et al., "*Oxidative Dimerization of Methane Over CaO Doped With Chlorides or Alkaline Metals,*" Catalysis Today, vol. 4, pp. 399-407 (1989).

Au, C.T. et al., "*The Characterization of BaF$_2$/Y$_2$O$_3$ Catalysts for the OCM Reaction,*" Journal of Catalysis, vol. 174, pp. 153-163 (1998).

Au, C.T. et al., "*The modification of Gd$_2$O$_3$ with BaO for the oxidative coupling of methane reactions,*" Applied Catalysis A, vol. 170, pp. 81-92 (1998).

Bloch, E.D. et al., "*Hydrocarbon Separations in a Metal-Organic Framework with Open Iron(II) Coordination Sites,*" Science, vol. 335, pp. 1606-1610 (2012).

Bostan, A.I. et al., "*Influence Of The Composition Of Perovskites Based In SrMnO$_3$ On Their Catalytic Properties In The Oxidative Coupling Of Methane,*" Theoretical and Experimental Chemistry, vol. 41 No. 1, pp. 32-36 (2005).

Burch, R. et al., "*Comparative Study of Catalysts for the Oxidative Coupling of Methane,*" Applied Catalysis, vol. 43, pp. 105-116 (1988).

Buyevskaya, O.V. et al., "*Transient Studies on Reaction Steps in the Oxidative Coupling of Methane over Catalytic Surfaces of MgO and Sm$_2$O$_3$,*" Journal of Catalysis, vol. 146, pp. 346-357 (1994).

Choudhary, V.R. et al., "*Beneficial Effect of Oxygen Distribution on Methane Conversion and C$_2$—Selectivity in Oxidative Coupling of Methane to C$_2$-Hydrocarbons over Lanthanum-promoted Magnesium Oxide.,*" Journal of the Chemical Society, Chemical Community, pp. 1526-1527 (1989).

Choudhary, V.R. et al., "*Factors influencing activity/selectivity of La-promoted MgO catalyst prepared from La- and Mg- acetates for oxidative coupling of methane,*" Fuel, vol. 79, pp. 1487-1491 (2000).

Dedov, A.G. et al., "*Oxidative coupling of methane catalyzed by rare earth oxides. Unexpected synergistic effect of the oxide mixtures,*" Applied Catalysis A, vol. 245, pp. 209-220 (2003).

Dissanayake, D. et al., "*Site Differentiation in Homolytic vs. Heterolytic Activation of Methane Over Ba/MgO Catalysts,*" Journal of Catalysis, vol. 146, pp. 613-615 (1994).

Driscoll, D.J. et al., "*Formation of Gas-Phase Methyl Radicals over MgO*" Journal of the American Chemistry Society, vol. 107, pp. 58-63 (1985).

Fomenko, E.V. et al. "*Physicochemical and catalytic properties of glass crystal catalysts for the oxidation of methane,*" Journal of Molecular Catalysis, vol. 158, pp. 209-214 (2000).

Fomenko, E.V. et al., "*Novel microdesign of oxidation catalysts. Part 1. Glass crystal microspheres as new catalysts for the oxidative conversion of methane,*" Catalysis Today, vol. 42, pp. 267-272 (1998).

Fomenko, E.V. et al., "*Novel microdesign of oxidation catalysts. Part 2. The influence of fluorination on the catalytic properties of glass crystal microspheres,*" Catalysis Today, vol. 42, pp. 273-277 (1998).

Gaffney, A.M. et al., "*Oxidative Coupling of Methane over Sodium Promoted Praseodymium Oxide,*" Journal of Catalysis, vol. 114, pp. 422-432 (1988).

Hong, J.H. et al., "*Oxidative coupling of methane over calcium chloride-promoted calcium chlorophosphate,*" Applied Catalysis A, vol. 205, pp. 253-262 (2001).

Ito, T. et al., "*Synthesis of ethylene and ethane by partial oxidation of methane over lithium-doped magnesium oxide,*" Nature, vol. 314, pp. 721-722 (1985).

Ito, T. et al., "*Oxidative Dimerization of Methane over a Lithium-Promoted Magnesium Oxide Catalyst,*" Journal of American Chemical Society, vol. 107, pp. 5062-5068 (1985).

Jones, C.A., et al., "*The Oxidative Conversion of Methane to Higher Hydrocarbons over Alkali-Promoted Mn/SiO2$_2$,*" Journal of Catalysis, vol. 103, pp. 311-319 (1987).

Keller, G.E. et al., "*Synthesis of Ethylene via Oxidative Coupling of Methane,*" Journal of Catalysis, vol. 73, pp. 9-19 (1982).

Kennedy, E.M. et al., "*Comparison of the oxidative dehydrogenation of ethane and oxidative coupling of methane over rare earth oxides,*" Applied Catalysis, vol. 75, pp. 321-330 (1991).

Krylov, O.V. "*Catalytic reactions of partial methane oxidation,*" Catalysis Today, vol. 18, pp. 209-302 (1993).

Labinger, J.A. "*Oxidative Coupling Of Methane: An Inherent Limit To Selectivity?*" Catalysis Letters. vol. 1, pp. 371-376 (1988).

Lapszewicz, J.A. et al., "*Investigation of reactivity and selectivity of methane coupling catalysts using isotope exchange techniques,*" Catalysis Letters, vol. 13, pp. 103-116 (1992).

Lee, J.S. et al., "*Oxidative Coupling of Methane to Higher Hydrocarbons,*" Catalysis Review—Scientific Engineering, vol. 30(2), pp. 249-280 (1988).

Lin, C. et al., "*Oxidative Dimerization of Methane over Lanthanum Oxide,*" Journal of Physical Chemistry, vol. 90, pp. 534-537 (1986).

Liu, S. et al., "*Methane Coupling Using Catalytic Membrane Reactors,*" Catalysis Reviews, vol. 43(1&2), pp. 147-198 (2001).

Lunsford, J.H. et al., "*The Effect of Chloride Ions on a Li$_+$– MgO Catalyst for the Oxidative Coupling of Methane,*" Journal of Catalysis, vol. 147, pp. 301-310 (1994).

Lunsford, J.H. "*The Catalytic Oxidative Coupling of Methane,*" Angewandte Chemie International, vol. 34, pp. 970-980 (1995).

Mleczko, L. et al., "*Catalytic oxidative coupling of methane—reaction engineering aspects and process schemes,*" Fuel Processing Technology, vol. 42, pp. 217-248 (1995).

Morales, E. et al., "*Oxidative Dehydrogenation of Ethane over a Lithium-Promoted Magnesium Oxide Catalyst,*" Journal of Catalysis, vol. 118, pp. 255-265 (1989).

Naito, S. "*Methane conversion by various metal, metal oxide and metal carbide catalysts,*" Catalysis Surveys From Japan, vol. 4, pp. 3-15 (2000).

Nelson, P. F. "*Isotopic Evidence for Direct Methyl Coupling and Ethane to Ethylene Conversion during Partial Oxidation of Methane over Li/MgO,*" Journal of Physical Chemistry, vol. 92, pp. 6176-6179 (1988).

Pak, S. et al., "*Elementary Reactions in the Oxidative Coupling of Methane over Mn/Na$_2$WO$_4$/SiO$_2$ and Mn/Na$_2$WO$_4$/MgO Catalysts,*" Journal of Catalysis, vol. 179, pp. 222230 (1998).

Palermo, A. et al., "*New efficient catalysts for the oxidative coupling of methane,*" Catalysis Letters, vol. 68, pp. 191-196 (2000).

(56) References Cited

OTHER PUBLICATIONS

Shigapov, A.N. et al., "Peculiarities In Oxidative conversion Of Methane To $C_2$ Hydrocarbons Over Cao-Cacl$_2$," React. Kinet. Catal. Lett., vol. 37, No. 2, pp. 397-402 (1988).

Sokolovoskii, V.D. "Oxidative dehydrodimerization of methane," Catalysis Today, vol. 14, pp. 415-465 (1992).

Sokolovoskii, V.D. et al., "Type Of Hydrocarbon Activation And Nature Of Active Sites Of Base Catalysts In Methane Oxidative Dehydrodimerization," Catalysis Today, vol. 4, pp. 293-300 (1989).

Stoukides, M. "Solid-Electrolyte Membrane Reactors: Current Experience and Future Outlook," Catalysis Review, vol. 42(1&2), pp. 1-70 (2000).

Tong, Y. et al., "Mechanistic and Kinetic Studies of the Reactions of Gas-Phase Methyl Radicals with Metal Oxides," Journal of American Chemical Society, vol. 113, pp. 4741-4746 (1991).

Tong, Y. et al., "Secondary Reactions of Methyl Radicals with Lanthanide Oxides: Their Role in the Selective Oxidation of Methane," Journal of Physical Chemistry, vol. 93, pp. 2896-2898 (1989).

Warren, B.K. "The Role of Chlorine in Chlorine-Promoted Methane Coupling Catalysts," Catalysis Today, vol. 13, pp. 311-320 (1992).

Zeng, Y. et al., "Oxidative coupling of methane on fluorite-structured samarium-yttrium-bismuth oxide," Applied Catalysis A. vol. 213, pp. 33-45 (2001).

Zhang, Q. et al., "Recent Progress in Direct Partial Oxidation of Methane to Methanol," Journal of Natural Gas Chemistry, vol. 12, pp. 81-89 (2003).

Olivier et al., "High-Temperature Parallel Screening of Catalysts for the Oxidative Coupling of Methane", Catalysis Today, 2008, vol. 137, pp. 80-89.

Tonkovich et al., "Enhanced C2 Yields from Methane Oxidative Coupling by Means of a Separative Chemical Reactor", Science, 1993, vol. 262, pp. 221-223.

Tonkovich et al., "A Simulated Countercurrent Moving-Bed Chromatographic Reactor for the Oxidative Coupling of Methane: Experimental Results", Chemical Engineering Science, 1994, vol. 49, pp. 4647-4656.

Liu et al., "Scale up and Stability Test for Oxidative Coupling of Methane Over Na2WO4-Mn/SiO2 Catalyst in a 200 ml Fixed-Bed Reactor", Journal of Natural Gas Chemistry, 2008, vol. 17m pp, 59-63.

Guo et al., "Energy-Efficient Coaromatization of Methane and Propane", Journal of Natural Gas Chemistry, 2009, vol. 18, pp. 260-272.

Guo et al., "Dehydrogenation and Aromatization of Propane Over Rhenium-Modified HZSM-5 Catalyst", Journal of Molecular Catalysis A: Chemical, 2005, vol. 239, pp. 222-227.

Ghose et al., "Oxidative Coupling of Methane Using Catalysts Synthesized by Solution Combustion Method: Catalyst Optimization and Kinetic Studies", Applied Catalysis A: General, 2014, vol. 472, pp. 39-46.

Ghose et al., Oxidative Coupling of Methane Using Catalysts Synthesized by Solution Combustion Method, Applied Catalysis A: General, 2013, vol. 452, pp. 147-154.

Choudhary et al., "Low-Temperature Nonoxidative Activation of Methane Over H-Galloaluminosilicate (MFI) Zeolite", Sciene, 1997, vol. 275, pp. 1286-1288.

Choudhary et al., "Simultaneous Conversion of Methane and Methanol into Gasoline Over Bifunctional Ga-, Zn-, In-, and/or Mo-Modified ZSM-5 Zeolites", Angewandte Chemie, 2005, vol. 44, pp. 4381-4385.

Anunziata et al., "Catalytic Conversion of Natural Gas with Added Ethane and LPG Over Zn-ZSM-11", Applied Catalysis A: General, 2000, vol. 190, pp. 169-176.

* cited by examiner pan# PROCESS AND CATALYST FOR METHANE CONVERSION TO AROMATICS

PRIORITY CLAIM

This application claims priority to and the benefit of U.S. Provisional Application No. 62/028,082, filed Jul. 23, 2014, which is incorporated by reference in its entirety.

FIELD OF INVENTION

The present invention relates to a process and catalyst system for the conversion of methane to $C_6$-$C_8$ aromatic hydrocarbons.

BACKGROUND OF INVENTION

Although methane is abundant, its relative inertness has limited its utility in conversion processes for producing higher-value hydrocarbons. For example, oxidative coupling methods generally involve highly exothermic and potentially hazardous methane combustion reactions, frequently require expensive oxygen generation facilities and produce large quantities of environmentally sensitive carbon oxides. In addition, non-oxidative methane aromatization is equilibrium-limited, and temperatures ≥ about 800° C. are needed for methane conversion greater than a few percent.

In the oxidative coupling of methane ("OCM"), methane and oxygen react at high temperatures over a catalyst to generate ethane as the primary product and ethylene as a secondary product; in the process, the methane feed and the products are partially oxidized to carbon monoxide and carbon dioxide. There are several drawbacks to the OCM reaction, such as low yields of ethane and ethylene (generally not more than about 25%) and a high amount of unreacted methane. Further, the OCM reaction is exothermic and has to be carefully operated to avoid potential runaways/explosions.

The OCM reaction is believed to start with the oxidative scission of one of the C—H bonds in methane leading to the formation of methyl radicals on the surface, followed by desorption and coupling in the gas phase to form ethane; ethane is in turn dehydrogenated by oxygen on the catalyst surface (and depending on temperature, non-oxidatively in the gas phase) forming ethylene. The inherent propensity of the $C_2$ products to oxidize limits the yields.

There have been two major technical hurdles to OCM commercialization: (i) low catalyst activity and selectivity and (ii) lack of catalyst stability at high temperature and steam partial pressure. Low catalyst activity requires higher operation temperatures (800-900° C.) and $O_2/CH_4$ ratios, resulting in lower C2 selectivity, higher exotherms and a more hazardous operation. Low catalyst selectivity translates into low carbon efficiencies and uneconomical recovery of ethane/ethylene from highly diluted streams. Lack of catalyst stability is a major barrier to the development of a practical process.

Another reaction in which methane is reacted to produce higher-value hydrocarbons is methane co-aromatization with higher alkanes and alkenes. In this reaction, methane is co-reacted with higher alkanes (typically ethane or propane), ethylene, propylene or alcohols to form a mixture of benzene, toluene and xylenes ("BTX"). As compared to methane aromatization, which is equilibrium-5 limited and only yields high conversions above 780° C., methane co-aromatization occurs at lower temperatures (500-700° C.) and achieves significantly higher methane conversion. For instance, when reacted alone, only 10-20% methane is converted to aromatics (80% selectivity, mostly benzene) at 785° C. By comparison, a 58/42 methane/ethane mixture can be transformed to BTX at 550° C. and 10-30% methane conversion; similarly, a 75/15 methane/propane mixture can be converted to BTX at 600° C. and 12-42% methane conversion. Higher methane conversions have been reported for the co-aromatization of methane/ethylene and methane/propylene mixtures and for the co-aromatization of methane and alcohols. The addition of the co-feed helps activate methane to the point that it is converted to a greater extent at much lower (up to 250° C. lower) temperatures. An example of methane co-aromatization is U.S. Pat. No. 5,936,135, which discloses reacting methane at a temperature in the range of 300° C. to 600° C. with (i) a C2-10 olefin and/or (ii) a C2-10 paraffin in the presence of a bifunctional pentasil zeolite catalyst, having strong dehydrogenation and acid sites, to produce aromatics. The preferred mole ratio of olefin and/or higher paraffin to methane and/or ethane in the feed ranges from about 0.05 to about 2.0.

OCM and methane co-aromatization may be integrated to produce higher yields of desired products, such as aromatics. In U.S. Pat. No. 5,336,825, a two-step process for the conversion of methane to liquid hydrocarbons in the gasoline range is disclosed. In the first step, methane and oxygen are converted to ethylene and lower olefins via OCM in one reactor and the product stream of the OCM reaction is catalytically converted to aromatics and other hydrocarbons in the gasoline range in a separate reactor. A process in which the OCM catalyst and aromatization catalyst were stacked within a single reactor was disclosed in Li et al. (Li et al., "Combined single-pass conversion of methane via oxidative coupling and dehydroaromatization," *Catalysis Letters*, vol. 89, pp. 275-279, 2003).

Of the aromatics, para-xylene is of particular value since it is useful in the manufacture of teraphthalic acid, a major component of polyester fibers and resins. Thus, commercially, once the aromatic mixture containing benzene, toluene, xylenes and heavier aromatics is produced, further processing is required to maximize para-xylene yields. Examples of such processes are benzene and/or toluene alkylation, toluene disproportionation and xylene isomerization. The catalysts used in at least some of these processes may be selectivated to increase the yield of para-xylene over other xylenes.

There is interest in developing alternative routes for the conversion of methane into aromatics and particularly routes that allow more methane to be incorporated into the aromatic product in a more efficient manner than the prior art processes. A process that controls the potential hazards of oxidative coupling of methane and utilizes the high amount of unconverted methane would be advantageous.

SUMMARY OF INVENTION

The current invention simplifies the traditional two (or more) step process for the production of aromatics to a single-step process by combining oxidative coupling of methane with methane co-aromatization with higher hydrocarbons in a single reaction stage. Methane and an oxidant may be partially converted to ethane and ethylene on an OCM catalyst component, and the OCM product intermediate comprising methane, ethane and ethylene may be subsequently converted into aromatics on an aromatization catalyst component. The reaction may be conducted at 550-850° C. and at about 50 psig (345 Kpa). The inventive process provides high yields of aromatics from methane.

The single-step process can be carried out in different types of reactor configurations: 1) a physical mixture of OCM and aromatization catalysts; 2) a stacked bed of OCM and aromatization catalysts; or 3) a hybrid OCM/aromatization catalyst. In one embodiment, a selectivated hybrid OCM-aromatization catalyst is used. The hybrid catalyst may be made by impregnating the OCM catalyst on the formulated zeolite catalyst or by dispersing the OCM catalyst within the pores of H-ZSM-5 and then formulating the catalyst into an extrudate. After formulation, the catalyst may be selectivated to increase para-xylene selectivity.

In an embodiment, a feed comprising methane and an oxidant is contacted with a catalyst having an OCM component and an aromatization component in a single reactor under conditions, including a temperature of about 600-800° C., effective to convert at least part of the methane in the feed to a product with at least 7 wt. % of aromatics, based on the weight of the product. At least part of the aromatics produced are then separated from the product. The OCM catalyst component comprises at least one alkaline/rare earth metal oxide and the aromatization catalyst component comprises at least one molecular sieve and at least one dehydrogenation metal.

The claimed process and catalyst used therein achieves high methane conversion at lower temperatures (less than 800° C.), higher methane incorporation into the aromatic product and significant reductions in production cost when compared to the traditional two (or more) step processes.

DETAILED DESCRIPTION

The current invention is directed to a single-step process and catalyst for the production of aromatics via oxidative coupling of methane and methane co-aromatization with higher hydrocarbons in a single reaction stage. The reaction may be conducted at 550-850° C., preferably 600-800° C., more preferably 600-750° C., and at about 50 psig (345 Kpa). The inventive process provides a product with at least 7 wt. % of aromatics, based on the weight of the product, from methane.

In the process, the first step is an OCM reaction in which methane and an oxidant are partially converted to ethylene and ethane on an OCM catalyst component. Typical ethylene/ethane molar ratios produced on the OCM catalyst are in the range of about 0.7-6.0 at about 20% methane conversion. Any suitable source of methane can be used in the present process, although a preferred source is natural gas, particularly wet natural gas, that is natural gas containing some or all of the higher hydrocarbons, particularly $C_2$ to $C_5$ hydrocarbon, coproduced with methane. A particularly preferred source of natural gas is shale gas. Using the present process, the complex and costly process of separating methane from the higher hydrocarbons present in natural gas can be obviated and the natural gas can be converted to easily transportable liquid hydrocarbons.

The oxidant is any oxygen-bearing material which, under the conditions in the reaction zone, yields an oxygen atom for the oxidative coupling. While not wishing to be limited to theory, the oxygen atom may be provided as reactive in a gaseous zone and/or may be provided on a catalyst surface as, for instance, reacted, absorbed, or adsorbed form. Convenient oxidants are normally gaseous such as molecular oxygen, air, ozone, and gases which yield oxygen such as $NO_2$, NO, $N_2O$, and peroxides such as $H_2O_2$. Materials that are liquid or solid at ambient conditions may also be used provided that they can be facilely introduced into the reaction zone. A redox mixed metal oxide that provides surface oxygen may also be used. Examples of such redox mixed metal oxides are oxides of Fe, Cr, Ni, Mn, and perovskites.

The methane and oxidant can be components of a feed mixture, which can further include diluent. Methane, oxidant, and optionally diluent can each be introduced into the reactor as one or more separate streams or as a premixed feed. The ranges given herein for methane and oxidant do not include diluents.

In one embodiment, methane and oxidant are provided to the reactor at a mole ratio of methane to oxidant of at least about 2:1. For example, the methane and oxidant are provided to the reactor at a mole ratio of alkane to oxidant of about 2:1 to about 50:1, alternatively at a mole ratio of about 2:1 to about 20:1.

The methane can comprise e.g., at least 30 mol % of the total feed provided to the reactor, based on total moles of the feed provided to the 5 reactor. For example, the methane can comprise at least 50 mol %, or at least 70 mol %, of the total feed provided to the reactor, based on total moles of the feed provided to the reactor. In certain embodiments, the methane comprises up to 98 mol % of the total feed provided to the reactor, based on total moles of the feed provided to the reactor. For example, the methane can comprise up to 90 mol % of the total feed provided to the reactor, based on total moles of the feed provided to the reactor.

The oxidizing component of the first mixture, e.g., oxidant, can comprise at least 2 mol % of the total feed provided to the reactor, based on total moles of the feed provided to the reactor. The oxidant can also comprise up to 20 mol % of the total feed provided to the reactor, based on total moles of the feed provided to the reactor.

In certain embodiments, the oxidant comprises at least 90.0 mol % of $O_2$, e.g., at least 99.0 mol % of $O_2$ based on the moles of the oxidant. The $O_2$ can be obtained or derived from air, e.g., by separation. Nitrogen obtained or derived from air can be utilized as a feed mixture diluent.

In certain embodiments, the feed provided to the hydrocarbon conversion process is comprised of at least 30.0 mol % methane and at least 2.0 mol % oxidant, the mole percent being based on total moles of the feed.

The feed streams can also be diluted e.g., with one or more diluents such as one or more inert materials. For example, the feed streams can be diluted with essentially inert fluid. Examples of inert fluid include, but are not limited to, steam, nitrogen, carbon dioxide or other fluids that are substantially unreactive with the hydrocarbon in the feed streams. When diluted, the diluent can provide from 5 mol % to 80 mol % of the feed streams, or from 10 mol % to 50 mol %, based on total moles of the feed streams. Dilution can be carried out by adding diluent to one or more of the reactants.

The OCM catalyst component consists of metal oxides, particularly rare earth/transition metal oxides, nitrates, carbonates, sulfates, phosphates, and mixtures thereof. The metal oxide catalysts also include mixed metal oxide catalysts, meaning that there may be more than one metal element in the oxide catalyst. Particularly useful metal oxide catalysts are metal oxide catalysts effective in catalytically converting alkane (e.g., methane) to C2+ olefin (e.g., ethylene).

An effective metal oxide catalyst can include at least one base metal of IUPAC Group 2, Group 3, Group 7, Group 8, Group 9, Group 14, Group 15 and the lanthanide series of metals. The metal oxide catalyst can additionally include at least one Group 1 metal. Examples of each these metals are shown in the PERIODIC CHART OF THE ELEMENTS, The Merck Index, 12th Ed., Merck & Co., Inc., 1996 ("Periodic Table").

Examples of Group 1 metals include Li, Na, K, Rb, Cs and Fr. Li, Na, K, Rb and Cs represent more common Group 1 metals.

Examples of Group 2 metals include Be, Mg, Ca, Sr, Ba and Ra. Mg, Ca, Sr and Ba are more common Group 2 metals.

Examples of Group 3 metals include Sc, Y, La and Ac. La is an example of a particularly common Group 3 metal.

Examples of Group 7 metals include Mn and Re. Mn is an example of a particularly common Group 7 metal.

Examples of Group 8 metals include Fe, Ru and Os. Fe is an example of a particularly common Group 8 metal.

Examples of Group 9 metals include Co, Rh and Ir. Co is an example of a particularly common Group 9 metal.

Examples of Group 14 metals include Sn and Pb. Pb is an example of a particularly common Group 14 metal.

An example of a Group 15 metal includes Bi.

Examples of the lanthanide series of metals include Ce, Pr, Nd, Sm, Eu, Gd, Tb, Dy, Ho, Er, Tm, Yb and Lu. Sm, Gd, Ho, and Yb are more common lanthanide metals.

Specific examples of oxidative coupling catalysts include those listed in U.S. Pat. No. 6,096,934. Such catalysts include lithium supported on magnesium oxide where the lithium is present in either the hydroxide or oxide form; bismuth supported on calcium oxide where the bismuth is present in either the hydroxide or oxide form; lithium supported on calcium oxide where the lithium is present in either the hydroxide or oxide form; cerium supported on magnesium oxide where the cerium is present in either the hydroxide or oxide form; nickel and lanthanum supported on magnesium oxide where the lanthanum is present in either the hydroxide or oxide form and the nickel is present in the metallic form; strontium supported lanthanum oxide where the strontium is present in either the hydroxide or oxide form; and lithium supported on lanthanum oxide where the lithium is present in either the hydroxide or oxide form; or any other metal or metal oxide or hydroxide catalyst promoted with a Group 1, 2, or lanthanide series element present in an oxide or hydroxide form.

U.S. Pat. No. 5,245,124 discloses an order of oxidative coupling catalysts first reported by Y. A. Amenomiya et al. in "Conversion of Methane by Oxidative Coupling," report to CANMET, Energy, Mines and Resources, Ottawa, Canada. The rating of catalysts is listed as follows: $Li/Sm_2O_3 > Na/CaO > K/CaO > LaAl_2O_3 > Sm_2O_3 > Li/CaO > PbO > Bi_2O_3 > Ho_2O_3 > Gd_2O_3 > Li/MgO > Li/CaO \sim Yb_2O_3 > Y_2O_3 Na/MgO \sim CaO > MgO$, in order of decreasing effectiveness for oxidative coupling. Additives to the catalysts include Ba, Li, Sr, Pb, K, Mg, Ca, Na, and Sb.

Perovskites of the structure $A_2B_2C_3O_{10}$ are also useful as catalysts for the oxidative coupling of lower alkane to heavier hydrocarbons. A is alkali metal; B is lanthanum or a lanthanide element, for example, cerium, neodymium, samarium, praseodymium, gadolinium or dysprosium; and C is titanium. A particular example is shown in U.S. Pat. No. 5,026,945, in which the perovskite is represented by the formula $A_xLn_yTi_zO_{10}$, wherein A is one or more alkali metal; Ln is one or more of lanthanum, cerium, neodymium, samarium, praseodymium, gadolinium and dysprosium; x is about 2; y is about 2; and z is about 3.

The OCM product intermediate comprising ethylene, ethane, and unreacted methane then reacts on the aromatization catalyst component. The aromatization catalyst component consists of a zeolite in the acidic form loaded with mixed metals, mixed metal/metal oxide, mixed metal oxides, or mixed metal/metal carbide/metal oxide.

In certain aspects, the aromatization catalyst component comprises at least one medium pore size molecular sieve having a pore size of about 5.3-5.7 Angstroms and a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48 and mixtures and intermediates thereof. ZSM-5 is described in detail in U.S. Pat. No. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In other aspects, the aromatization catalyst component employed in the present process comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of: molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire con 5 tent of which is incorporated as reference.); molecular sieves made from a common second degree building block, being a 2-dimensional tiling of such MWW framework topology unit cells, forming a monolayer of one unit cell thickness, preferably one c-unit cell thickness; molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as a molecular sieve component of the present catalyst.

In certain aspects, the molecular sieve employed in the present process may be an aluminosilicate or a substituted aluminosilicate in which part or all of the aluminum is replaced by a different trivalent metal, such as gallium or indium.

The invention can be practiced using catalysts that have been subjected to one or more catalyst treatments, e.g., selectivation. For example, the catalyst can comprise at least one molecular sieve which has been selectivated, either before introduction of the catalyst into the reactor or in-situ in the reactor, by contacting the catalyst with a selectivating agent, such as at least one organosilicon in a liquid carrier and subsequently calcining the catalyst at a temperature of 350 to 550° C. This selectivation procedure can be repeated two or more times and alters the diffusion characteristics of the catalyst such that the formation of paraxylene over other xylene isomers is favored. Such a selectivation process is described in detail in U.S. Pat. Nos. 5,633,417 and 5,675,047, the entire contents of which are incorporated herein by reference.

In addition to the molecular sieve component, the catalyst generally comprises at least one dehydrogenation component, e.g., at least one dehydrogenation metal. The dehydrogenation component is typically present in an amount of at least 0.1 wt. %, such as from 0.1 to 5 wt. %, of the overall catalyst. The dehydrogenation component can comprise one or more neutral metals selected from Groups 3 to 13 of the Periodic Table of the Elements, such as Ga, In, Zn, Sn, Cu, Re, Mo, W, La, Fe, Ag, Pt, Pd, and/or one or more oxides, sulfides and/or carbides of these metals. The dehydrogenation component can be provided on the catalyst in any manner, for example by conventional methods such as impregnation or ion exchange of the molecular sieve with a solution of a compound of the relevant metal, followed by conversion of the metal compound to the desired form, namely neutral metal, oxide, sulfide and/or carbide. Part or all of the dehydrogenation metal may also be present in the crystalline framework of the molecular sieve.

In one preferred embodiment, the bifunctional catalyst used in the present process is selected from the group consisting of Ga and/or Zn-modified ZSM-5 type zeolites such as Ga and/or Zn-impregnated H-ZSM-5, Ga and/or Zn-exchanged H-ZSM-5, H-gallosilicate of ZSM-5 type structure and H-galloaluminosilicate of ZSM-5 type structure. These zeolites can also be prepared by any suitable method, including conventional methods.

For example, the bifunctional catalyst may contain tetrahedral aluminum and/or gallium, which is present in the zeolite framework or lattice, and octahedral gallium or zinc, which is not present in the zeolite framework but present in the zeolite channels in close vicinity to the zeolitic protonic acid sites, and which is attributed to the presence of tetrahedral aluminum and gallium in the catalyst. The tetrahedral or framework Al and/or, Ga is responsible for the acid function of the catalyst and octahedral or non-framework Ga and/or Zn is responsible for the dehydrogenation function of the catalyst. In one preferred embodiment, the bifunctional catalyst comprises H-galloaluminosilicate of ZSM-5 type structure having framework (tetrahedral) Si/Al and Si/Ga mole ratios of about 10:1 to 100:1 and 15:1 to 150:1, respectively, and non-framework (octahedral) Ga of about 0.5 to 0 wt. %.

In addition to the molecular sieve components and dehydrogenation component, the catalyst may be composited with another material which is resistant to the temperatures and other conditions employed in the conversion reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active, may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, when the composite is prepared in the form of beads, in the range of about 2 to about 80 weight percent of the composite.

The combined one-step process provides many significant advantages over traditional aromatization processes and OCM or co-aromatization used alone. The inventive process achieves high methane conversion at lower reaction temperatures, i.e., less than 800° C. The ethylene and ethane intermediates, which are produced in the OCM reaction, activate the methane and enhance its reactivity to the aromatic products. Methane conversion is about 10-60% at less than 800° C. and the aromatic selectivity is about 60-95 wt %. The significant methane conversion into aromatic products eliminates the need for co-feeds as compared to co-aromatization standing alone. The primary aromatic products may further be converted to para-xylene by using a selectivated zeolite.

Feeds of various compositions can be used for this process. As described above, the base feed can be methane or wet natural gas. The methane/intermediate hydrocarbon molar ratio of the mixture reacting on the aromatization component depends on the intermediate composition resulting from the reaction on the OCM component, which in turn depends on the composition of the feed used. Product yields are also a strong function of the nature of the catalysts used (both the OCM and aromatization components), operation temperature/pressure and space velocity.

The single-step process of the current invention can be carried out in different types of reactor beds: 1) a physical mixture of OCM and aromatization catalysts; 2) a stacked bed of OCM and aromatization catalysts; or 3) a hybrid OCM-aromatization catalyst. In one embodiment, the OCM catalyst component and aromatization catalyst component are physically mixed within a single reactor. The physical mixture may be independent particles of OCM and aromatization catalysts mixed in various ratios, fine powders of OCM and aromatization catalysts having different sizes mixed and extruded into composite catalyst particles, or a combination of the two. One skilled in the art may determine the optimum ratios and powder particle sizes for the physical mixture.

In an embodiment, the OCM and aromatization catalyst components are layered, forming a stacked bed of catalyst within the reactor. The stacked bed may be a single layer of OCM catalyst component stacked on top of a layer of aromatization catalyst component or multiple layers of OCM catalyst component alternated with multiple layers of aromatization catalyst component. One skilled in the art may determine the optimum thickness and number of the layers. Preferably, the OCM catalyst component layer is thinner than the aromatization catalyst component layer and the stacked bed contains between 2 and 10 layers of each of the OCM catalyst component and aromatization catalyst component. One skilled in the art will be able to determine the optimum thickness of each of the layers. The oxidant may be introduced to the reactor at the top of the stacked bed, into only the top-most OCM catalyst layer, or staged to react with each OCM catalyst layer.

In another embodiment, a hybrid OCM-aromatization catalyst is used in which the OCM catalyst component is integrated with the aromatization catalyst component. The hybrid catalyst may be made by impregnating the OCM catalyst component on the formulated zeolite catalyst or by dispersing the OCM catalyst within the pores of H-ZSM-5 and then formulating into an extrudate. After formulation, the hybrid catalyst can be silica-selectivated to increase para-xylene selectivity, such as is described in detail in U.S. Pat. Nos. 5,633,417 and 5,675,047, the entire contents of which are incorporated herein by reference.

The hybrid catalyst has multiple advantages. The OCM reaction produces ethane and ethylene, which exist in their activated states for a short time before the reaction is complete. By conducting the OCM reaction within the zeolite having a dehydrogenation component, the activated ethane and ethylene may immediately react with the dehydrogenation component to form aromatics. Thus, less energy is needed for the reaction as compared to reacting fully formed ethane and ethylene produced in a separate reactor or in stacked beds of OCM and aromatization catalysts in a single reactor. Additionally, because the activated ethane and ethylene are in close proximity with the metal component (preferably Ga or Zn) of the aromatization catalyst, the ethane and ethylene are more likely to form aromatics than react with remaining oxygen from the OCM reaction to form carbon oxides.

A surprising and significant benefit of the hybrid catalyst is the ability to control the thermodynamics of the OCM reaction and drive the aromatization reactions forward. The highly endothermic aromatization reaction provides an internal quench of the highly exothermic OCM reaction; conversely, the high exotherm generated by the OCM reaction provides localized high temperature to drive the highly endothermic aromatization reaction. Such thermal coupling allows thermal efficiencies not available for existing aromatization processes while making the OCM reaction safer by reducing the potential for temperature runaways. Additionally, unreacted oxygen from the OCM reaction selectively reacts with hydrogen produced by aromatization to form water, shifting the equilibrium towards aromatics and increasing overall aromatics yields. This side reaction acts as a driver of the overall reaction and forces more methane to be converted; it also increases the local temperature, making aromatization more favorable.

The pore size of the zeolite is critical to the success of the reactions when a hybrid OCM-aromatization catalyst is used. It was surprisingly found that the metal dehydrogenation component of the aromatization catalysts must be in very close proximity to the OCM catalyst to allow the activated ethane and ethylene formed by OCM to react and form aromatics rather than reacting with oxygen to form carbon oxides. However, the pore size must be large enough to allow aromatics, and preferentially para-xylene, out of the pore. It has been found that a pore size of about 5.3-5.7 Å is preferred for the hybrid catalyst. A larger pore size does not allow specificity for para-xylene, while a smaller pore size produces olefins rather than aromatics. Examples of suitable zeolites are ZSM-5, ZSM-11, ZSM-12, ZSM-22, ZSM-23, ZSM-35, ZSM-48, and mixtures thereof. Further, within the optimum pore size range, the weight hourly space velocity (WHSV) can affect the distribution of aromatics to olefins produced; the preferred space velocity range depends on the catalyst, feed and temperature used. Production of aromatics is favored at lower space velocities, such as a WHSV lower than 25,000 $cm^3/g/h$, preferably lower than 15,000 $cm^3/g/h$, and more preferably lower than 5,000 $cm^3/g/h$. Production of olefins is favored at a WHSV of least 200 $cm^3/h/g$ of catalyst, such as at least 5,000 $cm^3/h/g$ of catalyst, for example at least 15,000 $cm^3/h/g$ of catalyst, preferably 15,000-25,000 $cm^3/g/h$.

The claimed process and catalyst used therein achieves high methane conversion at lower temperatures (less than 800° C.), higher methane incorporation into the aromatic product and significant reductions in production cost when compared to the traditional two (or more) step processes.

The description and examples above support one or more of the following more specific Embodiments.

Embodiment 1

A process for producing aromatics, the process comprising: providing a feed comprising methane and an oxidant; contacting the feed with a catalyst comprising an oxidative coupling of methane ("OCM") component and an aromatization component under conditions, including a temperature of about 600-800° C., effective to convert at least part of the methane in the feed to a product comprising at least 7 wt. % of aromatics, based on the weight of the product, wherein the OCM catalyst component and aromatization catalyst component are contained within a single reactor, wherein the OCM catalyst component comprises at least one alkaline/rare earth metal oxide, wherein the aromatization catalyst component comprises at least one molecular sieve and at least one dehydrogenation component; and separating at least part of the aromatics from the product.

Embodiment 2

The process of Embodiment 1, wherein the OCM catalyst component and the aromatization catalyst component are physically mixed within the reactor.

Embodiment 3

The process of Embodiment 1, wherein multiple layers of OCM catalyst component are alternated with multiple layers of aromatization catalyst component, forming a stacked bed of catalyst within the reactor.

Embodiment 4

The process of Embodiment 1, wherein the OCM catalyst component is integrated with the aromatization catalyst component to form a hybrid catalyst.

Embodiment 5

The process of any preceding Embodiment, wherein the molecular sieve comprises an aluminosilicate or a substituted aluminosilicate.

Embodiment 6

The process of any preceding Embodiment, wherein the molecular sieve has a pore size of about 5.3 to about 5.7 Angstroms.

Embodiment 7

The process of any preceding Embodiment, wherein the molecular sieve comprises ZSM-5 or ZSM-11.

Embodiment 8

The process of any preceding Embodiment, wherein the dehydrogenation component comprises a metal or compound thereof from Groups 3 to 13 of the Periodic Table.

Embodiment 9

The process of any preceding Embodiment, wherein the dehydrogenation component comprises a metal or compound selected from Ga, Zn, In, Sn, Cu, Re, Mo, W, La, Fe, Ag, Pt, Pd and mixtures thereof.

Embodiment 10

The process of any preceding Embodiment, wherein the alkaline earth/rare earth metal oxide is selected from the group consisting of Li-supported MgO, Bisupported CaO, Li-supported CaO, Ce-supported MgO, Ni/La-supported MgO, Sr-supported $La_2O_3$, Li-supported $La_2O_3$, and mixtures thereof.

Embodiment 11

The process of any preceding Embodiment, wherein the molecular sieve has been selectivated for para-xylene.

Embodiment 12

The process of any preceding Embodiment, wherein at least a part of the methane is derived from natural gas.

Embodiment 13

The process of any preceding Embodiment, wherein the oxidant is selected from the group consisting of $O_2$, air, ozone, peroxides, $NO_2$, NO, and $N_2O$.

Embodiment 14

A catalyst system for the production of aromatics comprising: an oxidative coupling of methane ("OCM") catalyst component comprising at least one alkaline/rare earth metal oxide; and an aromatization catalyst component comprising at least one molecular sieve and at least one dehydrogenation component; wherein the OCM catalyst component and aromatization catalyst component are contained within a single reactor.

Embodiment 15

The catalyst system of Embodiment 14, wherein the OCM catalyst component and the aromatization catalyst component are physically mixed within the reactor.

Embodiment 16

The catalyst system of Embodiment 14, wherein multiple layers of OCM catalyst component are alternated with multiple layers of aromatization catalyst component, forming a stacked bed of catalyst within the reactor.

Embodiment 17

The catalyst system of Embodiment 14, wherein the OCM catalyst component is integrated with the aromatization catalyst component to form a hybrid catalyst.

Embodiment 18

The catalyst system of Embodiment 17, wherein the OCM catalyst component is impregnated on the formulated molecular sieve.

Embodiment 19

The catalyst system of Embodiment 17, wherein the OCM catalyst component is dispersed within the pores of the molecular sieve prior to the molecular sieve being formulated into an extrudate.

Embodiment 20

The catalyst system of any of Embodiments 14-19, wherein the molecular sieve comprises an aluminosilicate or a substituted aluminosilicate.

Embodiment 21

The catalyst system of any of Embodiments 14-20, wherein the molecular sieve has a pore size of about 5.3 to about 5.7 Angstroms.

Embodiment 22

The catalyst system of any of Embodiments 14-21, wherein the molecular sieve comprises ZSM-5 or ZSM-11.

Embodiment 23

The catalyst system of any of Embodiments 14-22, wherein the dehydrogenation component comprises a metal or compound thereof from Groups 3 to 13 of the Periodic Table.

Embodiment 24

The catalyst system of any of Embodiments 14-23, wherein the dehydrogenation component comprises a metal or compound selected from Ga, Zn, In, Sn, Cu, Re, Mo, W, La, Fe, Ag, Pt, Pd and mixtures thereof.

Embodiment 25

The catalyst system of any of Embodiments 14-24, wherein the alkaline earth/rare earth metal oxide is selected from the group consisting of Li-supported MgO, Bi-supported CaO, Li-supported CaO, Ce-supported MgO, Ni/La-supported MgO, Sr-supported $La_2O_3$, Li-supported $La_2O_3$, and mixtures thereof.

Embodiment 26

The catalyst system of any of Embodiments 14-25, wherein the molecular sieve has been selectivated for para-xylene.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the enforceable scope of the present invention.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for producing aromatics, the process comprising:
   a. providing a feed comprising methane and an oxidant, wherein the feed has a mole ratio of methane to oxidant that is about 2:1 to about 20:1;
   b. contacting the feed with a catalyst comprising an oxidative coupling of methane ("OCM") component and an aromatization component under conditions, including a temperature of about 600-800° C., effective to convert at least part of the methane in the feed to a product comprising at least 7 wt. % of aromatics, based on the weight of the product, wherein the OCM catalyst component and aromatization catalyst component are physically mixed within a single reactor or the OCM catalyst component is integrated with the aromatization catalyst component to form a hybrid catalyst, wherein the OCM catalyst component comprises at least one alkaline/rare earth metal oxide, wherein the aromatization catalyst component comprises at least one molecular sieve and at least one dehydrogenation component; and
   c. separating at least part of the aromatics from the product.

2. The process of claim 1, wherein the molecular sieve comprises an aluminosilicate or a substituted aluminosilicate.

3. The process of claim 1, wherein the molecular sieve has a pore size of about 5.3 to about 5.7 Angstroms.

4. The process of claim 1, wherein the molecular sieve comprises ZSM-5 or ZSM-11.

5. The process of claim 1, wherein the dehydrogenation component comprises a metal or compound thereof from Groups 3 to 13 of the Periodic Table.

6. The process of claim 5, wherein the dehydrogenation component comprises a metal or compound selected from Ga, Zn, In, Sn, Cu, Re, Mo, W, La, Fe, Ag, Pt, Pd and mixtures thereof.

7. The process of claim 1, wherein the alkaline earth/rare earth metal oxide is selected from the group consisting of Li-supported MgO, Bi-supported CaO, Li-supported CaO, Ce supported MgO, Ni/La-supported MgO, Sr-supported $La_2O_3$, Li-supported $La_2O_3$, and mixtures thereof.

8. The process of claim 1, wherein the molecular sieve has been selectivated for paraxylene.

9. The process of claim 1, wherein at least a part of the methane is derived from natural gas.

10. The process of claim 1, wherein the oxidant is selected from the group consisting of $O_2$, air, ozone, peroxides, $NO_2$, NO, and $N_2O$.

11. A process for producing aromatics, the process comprising contacting a feed comprising methane and an oxidant with a catalyst comprising an oxidative coupling of methane ("OCM") component and an aromatization component under conditions, including a temperature of about 600-800° C., effective to convert at least part of the methane in the feed to a product comprising at least 7 wt. % of aromatics, based on the weight of the product;
   wherein the feed has a mole ratio of methane to oxidant that is about 2:1 to about 20:1;
   wherein the OCM catalyst component comprises at least one alkaline/rare earth metal oxide;
   wherein the aromatization catalyst component comprises at least one molecular sieve having pores and at least one dehydrogenation component; and
   wherein the OCM catalyst component is integrated with the aromatization catalyst component to form a hybrid catalyst by dispersing the OCM catalyst within the pores of the molecular sieve of the aromatization component and formulating the catalyst into an extrudate.

12. The process of claim 11, wherein the hybrid catalyst is selectivated to increase para-xylene selectivity.

13. The process of claim 11, further comprising recovering aromatics from the product.

14. The process of claim 11, wherein the molecular sieve comprises an aluminosilicate or a substituted aluminosilicate.

15. The process of claim 11, wherein the molecular sieve has a pore size of about 5.3 to about 5.7 Angstroms.

16. The process of claim 11, wherein the molecular sieve comprises ZSM-5 or ZSM-11.

17. The process of claim 11, wherein the dehydrogenation component comprises a metal or compound thereof from Groups 3 to 13 of the Periodic Table.

18. The process of claim 17, wherein the dehydrogenation component comprises a metal or compound selected from Ga, Zn, In, Sn, Cu, Re, Mo, W, La, Fe, Ag, Pt, Pd and mixtures thereof.

19. The process of claim 11, wherein the alkaline earth/rare earth metal oxide is selected from the group consisting of Li-supported MgO, Bi-supported CaO, Li-supported CaO, Ce supported MgO, Ni/La-supported MgO, Sr-supported $La_2O_3$, Li-supported $La_2O_3$, and mixtures thereof.

* * * * *